US006186986B1

(12) United States Patent
Berg et al.

(10) Patent No.: US 6,186,986 B1
(45) Date of Patent: *Feb. 13, 2001

(54) MICRO-CATHETERS AND METHODS OF THEIR MANUFACTURE

(75) Inventors: Todd Allen Berg, Lino Lakes; Jon Patrick St. Germain, Elk River, both of MN (US)

(73) Assignee: St. Jude Medical Cardiovascular Group, Inc., Minneapolis, MN (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/010,366

(22) Filed: Jan. 21, 1998

(51) Int. Cl.$^7$ ...................................................... A61M 5/00
(52) U.S. Cl. .......................... 604/264; 604/523; 604/524
(58) Field of Search ................................. 604/264, 523, 604/524, 525, 526, 527

(56) References Cited

U.S. PATENT DOCUMENTS

| 4,449,532 | 5/1984 | Storz ..................... 606/191 |
| 4,495,134 | 1/1985 | Ouchi et al. ............ 264/516 |
| 4,592,754 | 6/1986 | Gupta et al. .............. 623/1 |
| 4,638,667 | 1/1987 | Zimmer et al. ........ 73/432.1 |
| 4,739,768 | 4/1988 | Engelson ............... 128/658 |
| 4,748,984 | 6/1988 | Patel ...................... 128/658 |
| 4,817,601 | 4/1989 | Roth et al. .......... 128/303.1 |
| 4,850,351 | * 7/1989 | Herman et al. ......... 604/21 |
| 4,969,890 | 11/1990 | Sugita et al. .......... 606/192 |
| 5,125,895 | 6/1992 | Buchbinder et al. ... 604/95 |
| 5,167,686 | 12/1992 | Wong .................... 65/4.21 |
| 5,221,270 | * 6/1993 | Parker ................... 604/282 |
| 5,254,107 | 10/1993 | Soltesz ................. 604/282 |
| 5,269,757 | 12/1993 | Fagan et al. ........... 604/95 |
| 5,279,596 | 1/1994 | Castaneda et al. ..... 604/282 |
| 5,287,861 | 2/1994 | Wilk ...................... 128/898 |
| 5,297,564 | 3/1994 | Love .................... 128/898 |
| 5,342,299 | 8/1994 | Snoke et al. ........... 604/95 |
| 5,358,493 | * 10/1994 | Schweich, Jr. et al. .. 604/264 |
| 5,378,230 | * 1/1995 | Mahurkar ............... 604/43 |
| 5,383,852 | 1/1995 | Stevens-Wright ..... 604/95 |
| 5,423,311 | 6/1995 | Snoke et al. ............. 128/6 |
| 5,437,288 | 8/1995 | Schwartz et al. ..... 128/772 |
| 5,489,275 | * 2/1996 | Thompson et al. .... 604/264 |
| 5,522,834 | 6/1996 | Fonger et al. ......... 606/194 |
| 5,585,057 | * 12/1996 | Trota ..................... 264/130 |
| 5,599,324 | * 2/1997 | Mc Alister et al. .... 604/280 |
| 5,658,263 | * 8/1997 | Dang et al. ............ 604/280 |
| 5,662,622 | 9/1997 | Gore et al. ............. 604/282 |
| 5,674,197 | * 10/1997 | Van Muiden et al. . 604/282 |
| 5,676,659 | 10/1997 | McGurk ................. 604/282 |

FOREIGN PATENT DOCUMENTS

| 96/18361 | 6/1996 | (WO) ................. A61F/2/06 |
| WO 96/20750 | 7/1996 | (WO) ................ A61M/25/00 |

OTHER PUBLICATIONS

"Pebax® Resins, 33 Series Property Comparison," Technical Information, ATO Atochem Product Brochure, ATO Atochem (Dec. 1990).

"Fluoropolymer Heat Shrink Tubing," Zeus Product Brochure.

* cited by examiner

Primary Examiner—Wynn Wood Coggins
Assistant Examiner—Kevin C. Sirmons
(74) Attorney, Agent, or Firm—Fish & Neave; Robert R. Jackson; Breet G. Alten

(57) ABSTRACT

A micro-catheter including an inner primary liner and a plurality of concatenated tubes is provided. The primary liner extends substantially from the proximal end to the distal end of the catheter. Each of the tubes has a respective inner surface that is fused to the outer surface of the primary liner. For each and every pair of tubes, the outer diameter of the more proximally located tube is equal to or greater than the outer diameter of the more distally located tube. Each of the tubes may have different physical properties and dimensions for making customized micro-catheter profiles.

35 Claims, 3 Drawing Sheets

MICRO-CATHETERS AND METHODS OF THEIR MANUFACTURE

BACKGROUND OF THE INVENTION

This invention relates to medical catheters for accessing vascular target sites for diagnostic or intervention purposes. In particular, this invention relates to micro-catheters capable of navigating through extremely small diameter vessels.

Goldsteen et al. U.S. patent application No. 08/745,618, filed Nov. 7, 1996 (which is hereby incorporated by reference herein), shows medical procedures and instrumentation for installing tubular grafts in a patient (e.g., for providing a bypass conduit around a blockage in the patient's circulatory system). A key aspect of that invention involves using flexible catheters that are inserted into a patient's body through remote entry ports. These catheters must be capable of traveling relatively long distances, sometimes through circuitous, small diameter vessels (less than 2 millimeters), such as peripheral vasculature of the brain and heart. This environment, however, may cause a guide wire located in the micro-catheter to bind, or cause the micro-catheter itself to kink or buckle, which may prevent the catheter from reaching a target site in a patient.

In addition to guiding wires, micro-catheters may be used to inject viscous fluids, including drugs, to target sites in the patient. However, due to the viscous nature of some fluids and the small diameter of the lumen of the catheter, the fluid may be injected through the lumen at very high pressures, sometimes as high as 400 psi. Such pressures may cause the wall of the micro-catheter to rupture, or burst, which may harm the patient. Also, these fluids may be reactive with the inner surface of the flexible micro-catheter, which may cause rapid degradation of the catheter wall, thereby increasing the susceptibility of the wall to bursting.

In view of the foregoing, it is an object of this invention to provide a micro-catheter to access vascular target sites for diagnostic and interventional purposes.

It is another object of the invention to provide a micro-catheter with improved kinking and buckling resistance.

It is still another object of the invention provide a flexible micro-catheter with high burst strength and relatively low reactivity with reactive fluids.

It is a further object of the invention to provide a flexible micro-catheter with a high degree of steerability.

It is yet another object of the invention to provide methods of manufacturing a micro-catheter that has variable flexibility and profile along its length.

SUMMARY OF THE INVENTION

These and other objects of the invention are accomplished in accordance with the principles of the invention by providing a micro-catheter that includes a tubular primary liner that extends substantially along the entire length of the catheter and a plurality of concatenated tubular sections having inner surfaces that are fused to the outer surface of the primary liner. The outer diameter of any section is equal to or greater than the outer diameter of any other more distally located section. In a preferred embodiment of the present invention, a structural section, which extends substantially the entire length of the primary liner, is embedded between the primary liner and the tubular sections.

A method for making a micro-catheter in accordance with the principles of this invention is also provided. In a first step, a primary mandrel is covered with a tubular primary liner having an outer surface. Subsequently, a plurality of tubular sections are placed over the primary liner to form a concatenated chain of sections. Next, the outer surface of the primary liner is fused to the inner surfaces of the tubular sections and axially adjacent sections are fused to each other. Finally, the primary mandrel is removed from the primary liner to form a primary lumen. When a structural section is desired to improve the torque response, kink resistance, and burst resistance of the catheter, that structural section is preferably inserted between the primary liner and the tubular sections.

Further features of the invention, its nature and various advantages will be more apparent from the accompanying drawings and the following detailed description of the preferred embodiments.

BRIEF DESCRIPTION OF THE DRAWINGS

In FIG. 1A and several other FIGS., catheter width is greatly exaggerated compared to length to better reveal the construction of various catheter components.

DETAILED DESCRIPTION OF THE PREFERRED EMBODIMENTS

According to the present invention, a micro-catheter and methods for the manufacture and use of such a catheter are provided. The micro-catheter includes at least a primary liner and a plurality of concatenated tubular sections fused to the primary liner. A micro-catheter constructed in accordance with this invention may, for example, be used to guide instruments or fluids, or it may stand alone, for accessing particular vascular sites.

As used herein, a micro-catheter is a catheter for intra-vascular use, including coronary vessels, neuro-vessels, and/or neuro-vasculature. In contrast to a micro-catheter, a guiding catheter is not for intra-vascular use. A guiding catheter is larger than a micro-catheter and normally serves as a conduit for delivery of an interventional device, such as a micro-catheter, a guiding wire, or a balloon catheter, to targeted vasculature.

Figure 1A:
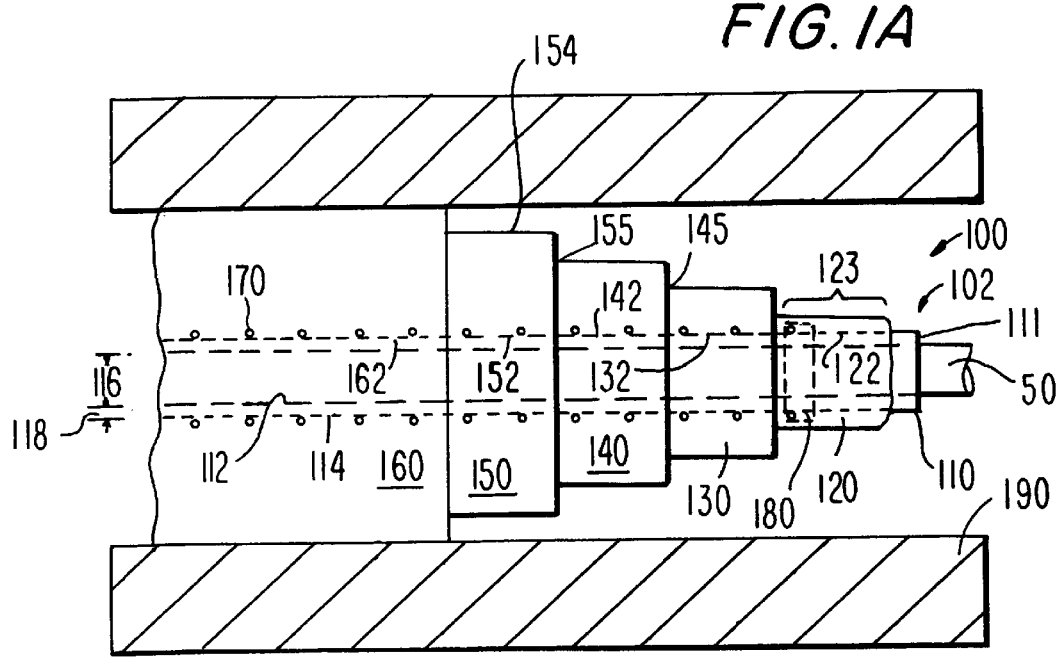
FIG. 1A is a simplified longitudinal view, partly in section, of a representative portion of an illustrative micro-catheter before being fused in accordance with this invention.
Figure 1B:
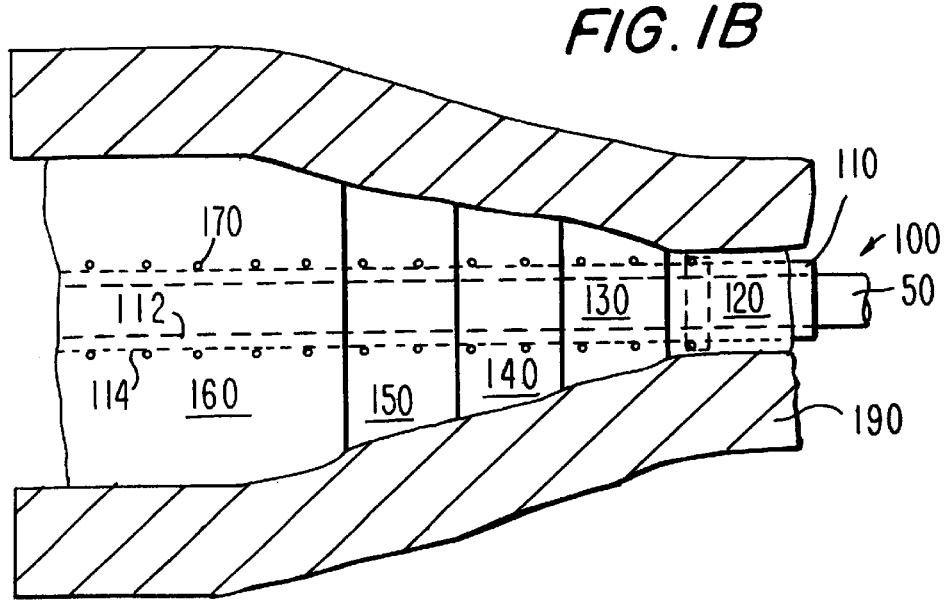
FIG. 1B is another view similar to FIG. 1A showing the same illustrative micro-catheter after being fused in accordance with this invention.

FIGS. 1A and 1B show micro-catheter 100 before and after fusing, respectively. Catheter 100 includes at least primary liner 110 and concatenated tubular sections 120, 130, 140, 150, and 160. Primary liner 110 extends substantially from the proximal end (not shown) of catheter 100 to distal end 102 of catheter 100 and has inner surface 112 and outer surface 114. Each of concatenated tubular sections 120, 130, 140, 150, and 160 has an inner surface 122, 132, 142, 152, and 162, respectively, that is fused to outer surface 114 of primary liner 110. The outer diameter of any section is equal to or greater than the outer diameter of any other more distally located section. In other words, given any pair of two sections, including a distal section and a proximal section (such as sections 120 and 130 and sections 120 and 160), the distal section has an outer diameter that does not exceed the outer diameter of the proximal section. The outer diameter of the distal section, however, should be equal to or less than the outer diameter of the proximal section of the pair. Micro-catheter 100, as shown in FIG. 1A, has five tubular sections 120, 130, 140, 150, and 160, but may, in accordance with this invention, have more or less sections, as required.

Primary liner 110 preferably has a substantially cylindrical shape. Primary liner 110 can be made from any flexible material, including many polymers. Polymers that may be used in accordance with this invention include polytetrafluoroethylene and (such as that sold under the trademark TEFLON® by E.I. du Pont de Nemours & Company, of Wilmington, Del.), polyetheramide (such as that sold under the trademark PEBAX®, by Ato Chemie, of Courbeboie, France), polyamide, polyimide, and any combination thereof.

The magnitude of inner diameter 116 of primary liner 110 depends on the particular application for which catheter 100 is used. However, inner diameter 116 can certainly range between about 0.010 inches and about 0.160 inches, preferably less than about 0.020 inches. Primary liner 110 preferably has a wall thickness 118 of between about 0.00075 inches and about 0.003 inches, but could be more or less as needed. Outer surface 114 of primary liner 110 is preferably roughened before being fused to inner surfaces 122, 132, 142, 152, and 162 to improve adhesion. Outer surface 114 may be roughened by etching it mechanically or chemically, but any roughening technique may be used. One type of chemical etching technique involves exposing surface 114 to tetrafluoroethylene (such as that sold under the trademark TETRA-ETCH®, by W. L. Gore & Associates, Inc., of Newark, Del.).

Sections 120, 130, 140, 150, and 160 may be made from any polymer capable of being molded when subject to elevated temperatures during fusing, including polytetrafluoroethylene, polyamide, polyimide, and preferably, polyetheramide.

As shown in FIG. 1A, micro-catheter 100 may further include structural section 170 disposed on outer surface 114 of primary liner 110 and substantially between outer surface 114 of primary liner 110 and sections 120, 130, 140, 150, and 160. Structural section 170 provides improved torque response, kink resistance, and burst resistance. Structural section 170 also provides a certain amount of rigidity to catheter to prevent collapse at sharp turns. Preferably, structural section 170 does not extend to distal end 102 of catheter 100 to form tip portion 123 without structural section 170 disposed thereunder. In this way, tip portion 123 remains very flexible. Although tip portion 123 may have any axial length, lengths between about 3 millimeters and about 10 millimeters have been found to work particularly well for many micro-catheter applications. Tip section 123 may have any useful outer diameter, and is preferably less than about 0.030 inches.

Structural section 170 may also have any appropriate wall thickness, but for many micro-catheter applications that thickness is preferably between about 0.001 inches and about 0.003 inches. In order to ensure proper fusing between outer surface 114 of primary liner 110 and the inner surfaces of the tubular sections, intervening structural section 170 should not prevent those surfaces from contacting with each other during fusing. Therefore, porous structural materials that provide contact between the layers and the liner during fusing, such as metal braid, coil, or ribbon, are appropriate structural materials. Structural section 170 may also be embedded directly in primary liner 110 before primary liner fused to the tubular sections.

A micro-catheter in accordance with this invention may further include an electromagnetically opaque material for determining the catheter position with electromagnetic radiation during use of the catheter. Preferably, electromagnetically opaque material is substantially opaque to electromagnetic radiation having a frequency in the x-ray portion of the electromagnetic spectrum. Examples of electromagnetically opaque materials include bismuth carbonate, tungsten, barium sulfate, and mixtures thereof.

In one embodiment of the present invention, the opaque material is a powder dispersed in at least one of the tubular sections. When the opaque material has a different concentration in each of the sections, the resulting opacity can be used to identify the exact positions of those sections during use. The electromagnetically opaque material may also be in the form of a solid marker attached to a known position on catheter 100. For example, as shown in FIG. 1A, marker 180 is placed on, or embedded in, section 120. Marker 180 may indicate the outer diameter of section 120 to prevent inserting a catheter too far. A plurality of markers can also be positioned along the catheter to identify multiple sections of the catheter during an operation.

Sections 120, 130, 140, 150, and 160 are made from flexible materials, preferably flexible polymers that are capable of being molded when subject to elevated temperatures during fusing, such as polytetrafluoroethylene, polyamide, polyimide, and polyetheramide. Polyetheramide is a preferred polymer because its physical characteristics, including hardness, tensile strength, and flexural modulus, can be engineered by choosing the proper ratio of (1) regular and linear chains of rigid polyamides to (2) flexible polyethers. For example, in order to obtain a micro-catheter having a flexibility that increases distally, the polyamide-polyether concentration ratio should decrease distally. In other words, the concentration ratio of any proximal section should not be less than the concentration ratio for any other more distal section.

In a similar fashion, other physical properties of the micro-catheter can be varied axially. For example, if the hardness of a catheter should decrease distally, the hardness of any distal section should not exceed the hardness for any other more proximal section of course, a single section can have a hardness that decreases distally as well, either in a step-wise fashion or continuously. In addition to hardness, the flexural modulus of the catheter will decrease distally when the flexural modulus of any distal section does not exceed the flexural modulus of any other more proximal section. And, like hardness, a single section can have a flexural modulus that varies (especially decreases) distally, either in a step-wise fashion or continuously, if originally formed that way. Furthermore, as shown clearly in FIG. 2, the length of each successive section may decrease (or increase) in a distal direction.

The following table describes some physical properties of the illustrative example according to the present invention shown in FIGS. 1A and 1B:

EXAMPLE

| Section No. | Flexural Modulus Range (kpsi) | Hardness (D) | Radial Dimensions (inner × outer diameter (inches)) | Length (cm) |
|---|---|---|---|---|
| 120 | 2–3 | 40 | 0.023 × 0.026 | 1 |
| 130 | 3–13 | 55 | 0.023 × 0.028 | 3 |
| 140 | 13–29 | 63 | 0.023 × 0.031 | 7 |
| 150 | 29–50 | 67 | 0.023 × 0.033 | 20 |
| 160 | >50 | 70–80 | 0.023 × 0.039 | 94 |

Figure 2:
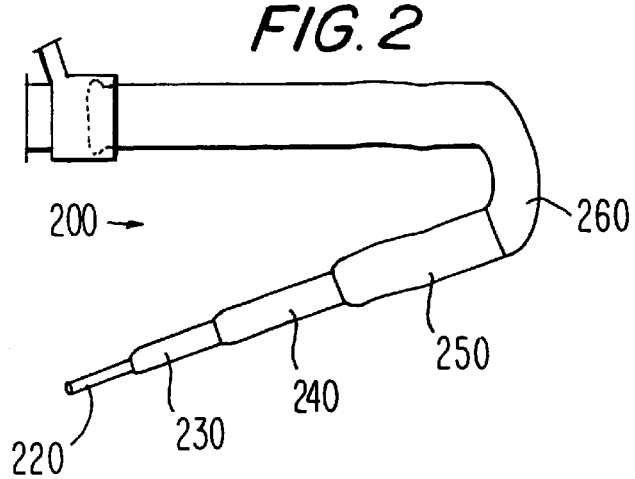
FIG. 2 is a longitudinal elevational view of a portion of another illustrative micro-catheter having a curved section in accordance with this invention.
Figure 3:
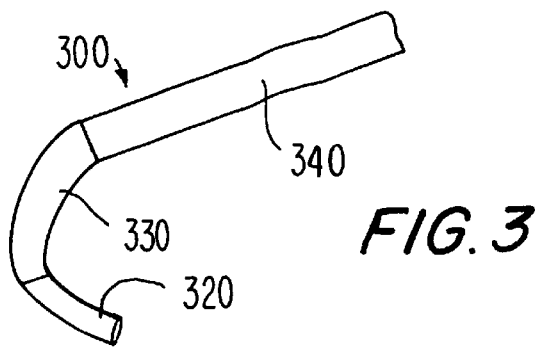
FIG. 3 is a longitudinal elevational view of a portion of another illustrative micro-catheter having several curved sections in accordance with this invention.

In order to improve the steerability of a micro-catheter according to this invention, at least one of the tubular sections may be curved. The curvature improves steerability because when catheter is rotated in a vessel, for example, the catheter tip can be pointed in any desired angular direction. For example, FIG. 2 shows micro-catheter 200, including sections 220, 230, 240, 250, and 260, of which section 260 is curved. FIG. 3 shows micro-catheter 300, including 320, 330, and 340, of which sections 330 and 340 are curved. The curved sections are formed by heating the micro-catheter around a curved mandrel. Curvature may be accomplished by inserting a curved mandrel into a prefused catheter and applying heat to reshape the catheter. Alternatively, the catheter may be formed during the initial fusing process with a curved primary mandrel. Furthermore, a catheter that is curved and braided provides steerability and torque such that a guide wire is not always required.

In addition to the primary mandrel, one or more secondary mandrels may be used to form respective integrated secondary lumen, as described more fully in Berg et al. U.S. application No. 09/010,367, filed Jan. 21, 1998 (Docket No. 293/032), which is hereby incorporated by reference herein. A secondary lumen may be integrated into one or more contiguous sections and form an opening at any position along the length of the catheter.

Figure 5:
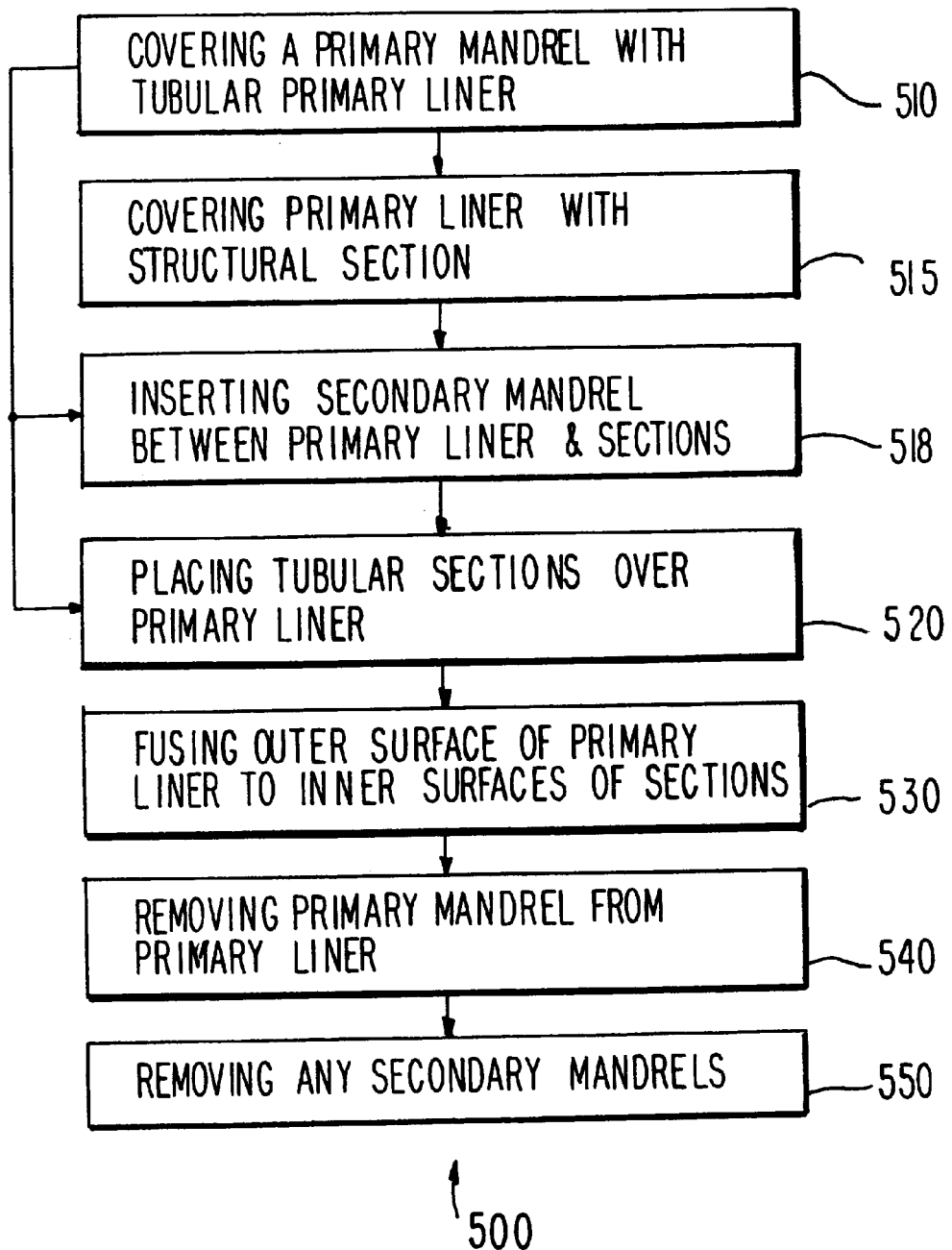
FIG. 5 is a flow chart of an illustrative embodiment of the procedure for manufacturing a micro-catheter according to this invention.

FIG. 5 shows an illustrative sequence of steps 500 for manufacturing a catheter in accordance with this invention, such as micro-catheters 100, 200, and 300, shown in FIGS. 1B, 2, and 3, respectively. These steps include covering a primary mandrel with a tubular lining in step 510, placing or sliding a plurality of tubular sections over said primary liner in step 520, fusing the primary lining and tubular sections in step 530, and removing the primary mandrel from the primary liner to form a primary lumen therein in step 540. To some extent these steps have already been mentioned, so the discussion of them here may be some what abbreviated.

In step 510, a primary mandrel is covered with a tubular primary liner. Primary mandrel 50 may be cylindrical and have any outer diameter. However, preferred embodiments of the invention are formed using a primary mandrel with an outer diameter of up to about 0.020 inches. The primary mandrel may be covered by vapor deposition or sliding the primary liner onto the primary mandrel. In order to improve the fused bond between the inner surface of the tubular sections and the outer surface of the primary liner during fusing, in step 530, the outer surface of the primary liner may be roughened, such as by etching, by any conventional mechanical or chemical technique.

In step 520, a plurality of tubular sections are placed over the primary liner to form a concatenated chain of sections. Each of the sections has an inner surface and an outer diameter. Furthermore, given any two sections, including a distal section and a proximal section, the distal section has an outer diameter that does not exceed the outer diameter of the proximal section. The outer diameter of the distal section, however, may be equal to or less than the outer diameter of the more proximal section.

Figure 4A:
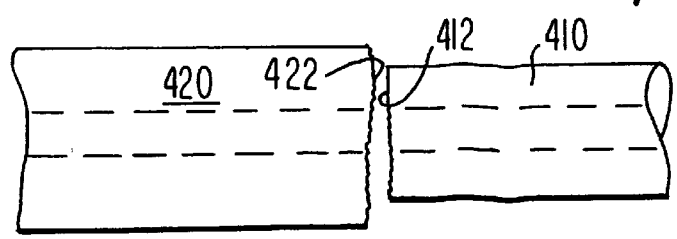
FIG. 4A is a longitudinal view of two adjacent sections, with roughened ends, of still another illustrative micro-catheter in accordance with this invention.
Figure 4B:
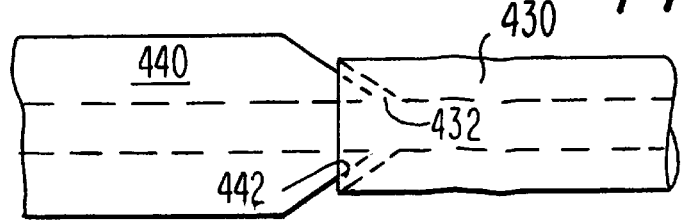
FIG. 4B is a longitudinal view of two adjacent sections, with shaped ends, of yet another illustrative micro-catheter in accordance with this invention.

The axial ends of each tubular section may be shaped or roughened to improve the fused bond between adjacent sections. For example, FIG. 4A shows an illustrative embodiment according to this invention in which contacting surfaces 412 and 422 of adjacent sections 410 and 420 are roughened before fusing. FIG. 4B shows another illustrative embodiment in which portions of contacting surfaces 432 and 434 of respective sections 430 and 440 are shaped to axially overlap. This overlap increases the surface area, which may improve the fused bond therebetween.

In step 515, the primary liner may optionally be covered with a porous structural section that permits contact during fusing between the outer surface of the primary liner and the inner surfaces of the tubular sections. As described in some detail above, the structural section provides improved torque response, kink resistance, and burst resistance.

In step 518, a secondary mandrel may optionally be inserted between the primary liner and the tubular sections before being fused together to form an integrated secondary lumen upon removal of the secondary mandrel in step 550. Preferably, the secondary mandrel is first coated with a secondary liner, which may be made from the same material as the primary liner. Inserting a secondary mandrel in step 518 preferably includes placing the distal end of the secondary mandrel at a surface of the catheter to form a secondary lumen opening. That opening may be at a tubular section outer surface (such as outer surface 154 of section 150), a tubular section distal surface (such as distal surface 145 of section 140), a primary liner inner surface (such as inner surface 112), or a primary liner distal surface (such as distal surface 111). The secondary lumen opening may also be formed at the intersection between any two adjacent section outer surfaces (such as at point 155 between sections 140 and 150). As described more fully in the above-mentioned Berg et al. reference, an inflatable balloon may be formed at an outer surface opening by bonding with an elastic sheet over that opening.

In step 530, the inner surfaces of the tubular sections are fused to the outer surface of the primary liner and axially adjacent sections are fused to each other. Step 530 may include (1) placing heat shrink tubing over the chain of concatenated sections, (2) heating the heat shrink tubing so that it squeezes together the primary liner (and any secondary liners) and the tubular sections, and (3) removing the heat shrink tubing after the heating step. Fusing may further include heating the primary liner via the primary mandrel. Finally, in step 540, the primary mandrel is removed from the primary liner to form a primary lumen.

It will be understood that the foregoing is only illustrative of the principles of the invention, and that various modifications can be made by those skilled in the art without departing from the scope and spirit of the invention. For example, the number of sections, as well as the material properties and physical dimensions, may be selected as needed.

What is claimed is:

1. A micro-catheter having a proximal end and a distal end, said micro-catheter comprising:

a tubular primary liner that substantially extends from said proximal end to said distal end, said primary liner having an inner surface and an outer surface; and a plurality of concatenated tubes having respective inner surfaces fused to said primary liner outer surface, such each and every pair of said tubes comprises a proximal tube having an outer diameter and a distal tube having an outer diameter that does not exceed said outer diameter of said proximal tube and wherein at least one of said each and every pairs comprises a respective proximal tube and a respective distal tube such that an outer diameter of said respective distal tube is less than an outer diameter of said respective proximal tube.

2. The micro-catheter of claim 1 wherein each of said tubes comprises a polymer.

3. The micro-catheter of claim 2 wherein each of said tubes has a hardness, said distal tube hardness not exceeding said proximal tube hardness.

4. The micro-catheter of claim 3 wherein at least one of said tubes has a hardness that decreases distally.

5. The micro-catheter of claim 4 wherein said at least one of said tubes has a hardness that continuously decreases distally.

6. The micro-catheter of claim 2 wherein said polymer comprises polyetheramide having a polyether concentration and an polyamide concentration at a polyether-polyamide ratio, wherein said ratio for said proximal tube is not less than said ratio for said distal tube.

7. The micro-catheter of claim 1 wherein each of said tubes has a flexural modulus, said distal tube flexural modulus not exceeding said proximal tube flexural modulus.

8. The micro-catheter of claim 7 wherein said tubes include a tip section, said tip section being closest to said distal end of said catheter, said tip section outer diameter being less than about 0.030 inches.

9. The micro-catheter of claim 8 wherein at least one of said tubes has an outer diameter that decreases distally.

10. The micro-catheter of claim 9 wherein said at least one of said tubes has an outer diameter that continuously decreases distally.

11. The micro-catheter of claim 1 further comprising a structural tube disposed on said outer surface of said primary liner for providing torque response, kink resistance, and burst resistance to said catheter.

12. The micro-catheter of claim 11 wherein said structural tube comprises a structural material.

13. The micro-catheter of claim 12 wherein said structural material is metal.

14. The micro-catheter of claim 13 wherein said structural material is selected from a group consisting of braided, coiled, and ribboned materials.

15. The micro-catheter of claim 11 wherein a distal most tube has a distally located tip portion, said structural tube being disposed on said primary liner up to a proximal end of said tip portion so that said tip portion has a desired stiffness.

16. The micro-catheter of claim 15 wherein said tip portion has an axial length of between about 3 millimeters and about 10 millimeters.

17. The micro-catheter of claim 11 wherein said structural tube is substantially between said outer surface of said primary liner and said tubes.

18. The micro-catheter of claim 11 wherein said structural tube has a wall thickness of between about 0.001 inches and about 0.003 inches.

19. The micro-catheter of claim 1 wherein said electromagnetically opaque material is substantially opaque to electromagnetic radiation having a frequency in the x-ray portion of the electromagnetic spectrum.

20. The micro-catheter of claim 19 wherein said electromagnetically opaque material is selected from a group consisting of bismuth carbonate, tungsten, barium sulfate, and mixtures thereof.

21. The micro-catheter of claim 19 wherein said opaque material is a solid marker attached to a known position of said catheter.

22. The micro-catheter of claim 19 wherein said opaque material is a powder dispersed in at least one of said tubes.

23. The micro-catheter of claim 22 wherein said opaque material has a different concentration in each of said at least one tubes for identification purposes during use of said catheter.

24. The micro-catheter of claim 1 wherein said catheter has an integrated secondary lumen.

25. The micro-catheter of claim 24 wherein said secondary lumen is at least partially formed in one of said tubes.

26. The micro-catheter of claim 25 wherein at least two of said adjacent tubes at least partially overlap.

27. The micro-catheter of claim 1 wherein said primary liner comprises a material selected from a group consisting of polytetrafluoroethylene, polyamide, polyimide, polyetheramide, and any combination thereof.

28. The micro-catheter of claim 1 wherein said primary liner has an inner diameter of less than about 0.020 inches.

29. The micro-catheter of claim 1 wherein said primary liner has a wall thickness of between about 0.00075 inches and about 0.003 inches.

30. The micro-catheter of claim 1 wherein said primary liner outer surface is roughened.

31. The micro-catheter of claim 1 further comprising an electromagnetically opaque material for determining a position of said catheter with electromagnetic radiation during catheter use.

32. The micro-catheter of claim 1 wherein each of said tubes has a length, said distal tube length not substantially exceeding said proximal tube length.

33. The micro-catheter of claim 1 wherein at least one of said tubes has a flexural modulus that decreases distally.

34. The micro-catheter of claim 33 wherein said at least one of said tubes has a flexural modulus that continuously decreases distally.

35. The micro-catheter of claim 1 wherein at least one of said plurality of tubular tubes is curved to improve steerability.

* * * * *